(12) United States Patent
Ortega et al.

(10) Patent No.: US 7,028,535 B2
(45) Date of Patent: Apr. 18, 2006

(54) SYSTEM AND METHOD FOR DETECTING AND MEASURING LIQUID CARRY OVER IN A GAS STREAM

(75) Inventors: Pedro Ortega, Los Teques (VE); Gonzalo Chinea, Miranda (VE)

(73) Assignee: Intevep, S.A., Caracas (VE)

( * ) Notice: Subject to any disclaimer, the term of this patent is extended or adjusted under 35 U.S.C. 154(b) by 77 days.

(21) Appl. No.: 10/832,896

(22) Filed: Apr. 27, 2004

(65) Prior Publication Data

US 2005/0235738 A1   Oct. 27, 2005

(51) Int. Cl.
*G01N 1/00* (2006.01)
(52) U.S. Cl. .................................. 73/53.01; 73/28.05
(58) Field of Classification Search ............. 73/28.05, 73/861.43, 861.73, 863.22, 865.5
See application file for complete search history.

(56) References Cited

U.S. PATENT DOCUMENTS

| | | | | |
|---|---|---|---|---|
| 3,926,271 | A | * | 12/1975 | Patashnick .............. 177/210 R |
| 4,305,450 | A | * | 12/1981 | van der Linden et al. .......... 164/150.1 |
| 4,674,337 | A | * | 6/1987 | Jonas ...................... 73/861.73 |
| 5,681,986 | A | * | 10/1997 | Merk et al. ................. 73/61.75 |
| 6,502,450 | B1 | * | 1/2003 | Patashnick et al. ......... 73/23.21 |
| 6,565,638 | B1 | * | 5/2003 | Sugita et al. ................. 96/413 |
| 2001/0007210 | A1 | * | 7/2001 | Muller et al. ................. 73/579 |
| 2002/0134137 | A1 | * | 9/2002 | Ondov et al. ............... 73/28.05 |

\* cited by examiner

*Primary Examiner*—Charles Garber
(74) *Attorney, Agent, or Firm*—Bachman & LaPointe, P.C.

(57) ABSTRACT

A system for automatically detecting liquid carry over in a gas stream includes a sample line communicated with the gas stream for separating a sample of the gas stream; and an impactometer positioned along the line for being impacted by the sample, and for generating a signal indicative of sample density.

3 Claims, 1 Drawing Sheet

SYSTEM AND METHOD FOR DETECTING AND MEASURING LIQUID CARRY OVER IN A GAS STREAM

BACKGROUND OF THE INVENTION

The invention relates to a system and method for automatically detecting and/or measuring liquid carryover in gas streams.

Gas pipelines are widely used for conveying fuels and the like to areas to where they are to be processed, stored, used or the like.

Such pipelines experience potentially serious problems when liquid is carried over into the gaseous streams carried into the pipeline. In typical hydrocarbon producing and processing methods, however, such liquid does tend to wind up in the gaseous stream. This can cause failure in various gas handling equipment, and is an expensive problem to correct.

Conventionally, in order to determine if liquid is present in the stream, a paper is positioned in the stream which shows the presence of liquid. Such a system does not provide accurate-real time data as to the amount of liquid in the stream, and is accompanied by problems and hazards in connection with the technique itself as well. Further, the paper must be measured, and data sent to a central control area where, finally, some steps can be taken on the basis of this less-than-accurate information to attempt to resolve same. In the meantime, while this is being done, liquid is being fed through the gas pipeline for example to gas compressors and the like, and such hardware can be destroyed. Costs for correcting these problems are significant.

It is clear that the need remains for an improved method to detect and measure liquid in a gaseous stream.

It is therefore the primary object of the present invention to provide a system for detecting liquid carryover in a gas stream.

It is a further object of the present invention to provide a method for detecting liquid carryover in a gas stream.

Other objects and advantages of the present invention will appear hereinbelow.

SUMMARY OF THE INVENTION

In accordance with the present invention, the foregoing objects and advantages have been readily attained.

According to the invention, a system is provided for detecting liquid carryover in a gas stream, which system comprises a sample line communicated with the gas stream for separating a sample of said gas stream, and an impactometer positioned along said sample line for being impacted by said sample, and for generating a signal indicative of sample density.

In further accordance with the invention, a method is provided for detecting liquid carryover in a gas stream, which method comprises the steps of obtaining a sample stream from said gas stream; flowing said sample stream to an impactometer positioned along said sample line for being impacted by said sample, and for generating a signal indicative of sample density; and determining an amount of liquid in said sample stream from said signal.

BRIEF DESCRIPTION OF THE DRAWINGS

A detailed description of preferred embodiments of the present invention follows, with reference to the attached drawings, wherein.

DETAILED DESCRIPTION

The invention relates to a system and method for automatically detecting and/or measuring liquid carryover in a gas stream.

Hydrocarbon gas streams and the like may at times be two-phase streams, including gas and some liquid. This liquid can cause potentially serious problems. A method for detecting the presence of liquid and also for sensing an amount of liquid in the stream are therefore valuable, and are provided in accordance with the present invention.

According to the invention, it has been found that the two-phase gas stream, including liquid, can be impacted against a suitable impactometer which can be based upon a conventional pressure transducer. The signal can be used to determine whether and how much liquid has been carried over.

According to the invention, this system and method are carried out by obtaining a sample from the gas stream, and communicating this sample of the gas stream to an impactometer whereby the impact of the sample against the impactometer generates a signal which is functionally related to the density of the fluid. Of course, this density can be used to detect and measure the presence of liquids.

Still further according to the invention, it may be desirable to obtain a separated and substantially liquid-free sample of the gas, and to impact this gas stream against an impactometer preferably the same impactometer, so as to obtain a base line signal against which the signal from the two-phase sample can be compared.

Figure 1:
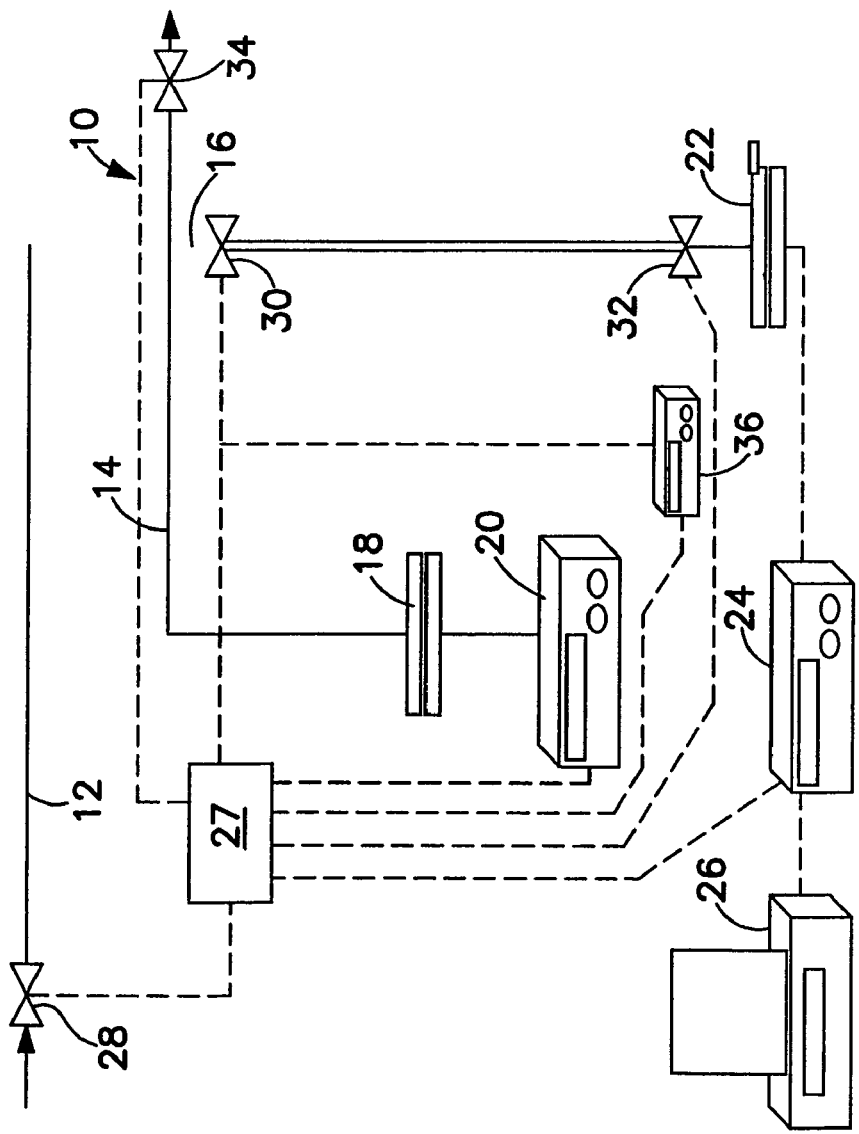
FIG. 1 schematically illustrates a system in accordance with the present invention.

FIG. 1 illustrates a system 10 in accordance with the present invention.

According to the invention, an admission line 12 typically carries the fluid from a gas pipeline or the like. This fluid may be entirely gas, or may be a substantially two-phase fluid containing liquid as well. As set forth above, it is the object of the present invention to detect and determine how much liquid is present in this stream.

Admission line 12 feeds to measuring branch 14 for measuring entrance pressure and to a sample tubing branch 16. In measuring branch 14, the stream is exposed to a normal pressure transducer 18, and results are fed to a suitable digital indicator 20 or the like. Results can also be fed to a suitable control system 27 to register and stock or store entrance pressure.

At the same time, a sample is fed to sample branch 16, wherein a sample is fed through an impactometer 22.

In accordance with the present invention, the difference in signal from base line and sample line can be utilized, particularly by calibrating against the baseline signal, to detect the presence of liquid and, in many instances, to determine how much liquid is present in the stream. This is particularly true when the types of liquid which can be present in the stream are known, such that the density can readily be transformed into an amount of liquid of substantially known density.

According to the invention, it can be possible to calibrate the system in an alternate way. This alternate approach involves using a well-known inner gas which is tested with the impactometer. In this manner, a signal is obtained which is functionally related to the density of the gas used at the conditions used (P,t). In this way, the impactometer is calibrated to obtain, through this functional relationship, the density and amount of liquid present in the gas phase.

With impactometer calibration data obtained as set forth above, either with a sample of active gas being measured or with inert gas having known properties at known conditions, the signal obtained using the impactometer can readily be corrected with a fluid sample density measurement as desired.

Signals from impactometer 22 are also fed to a suitable digital indicator 24 as shown, and this information can be fed for example to a paper register 26 and/or to various computerized control systems and the like. In this regard, a suitable control system or unit 27 could advantageously be communicated with valves for system 10, for example valves 28, 30, 32 and 34 as shown in FIG. 1 for controlling when and how to obtain and test a sample as discussed above. Data collected by the control unit can then be used to determine what other actions, if any, must be taken. Control unit 27 is operationally associated with various components of the system so as to accept data for processing and/or storage, and to emit signals to order operations and control such other components.

Also as shown, in FIG. 1, it may desirable to locate a suitable measuring device such as digital thermometer 36 for obtaining additional data as to the baseline and sample measurement which is useful in further calculation of measurements obtained with impactometer 22, and this data can also be communicated to control unit 27.

From a consideration of the system of FIG. 1, it should readily be appreciated that this system can easily be communicated with any gas pipeline, and therefore can be used for measurement of all existing and new equipment as well, thereby providing a very reliable and accurate method for detecting and measuring the amount of liquid contained in a gas pipeline. This allows steps to be taken to avoid the above-mentioned significant damage and costs incurred in connection with liquid carryover.

Figure 2:
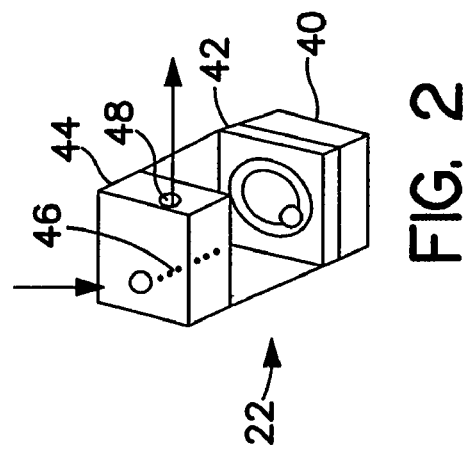
FIG. 2 schematically illustrates a preferred transducer for use in accordance with the present invention.

Turning to FIG. 2, a preferred embodiment of an impactometer is illustrated. FIG. 2 shows impactometer 22 having a base member 40, a diaphragm 42 containing the conventional elements of a typical pressure transducer, but modified with a top member 44 having an inlet path 46 which is positioned so as arrange the flow through path 46 substantially perpendicular to a diaphragm 42 which is to be impacted by the flow. Inlet plate 44 further has an outlet path 48 for carrying the sample away from diaphragm 42 after the impact has been made.

In a manner which is well known to a person of ordinary skill in the art, diaphragm 42 and the components associates with same detect differences in pressure applied to diaphragm 42 by the impact of the gaseous stream, which can be used to generate a signal from which fluid density and, accordingly, presence of liquid, can be determined.

The structure of flow paths of inlet plate 44 is advantageous in accordance with the present invention since the position and location of these flows paths avoid collection of liquid at the surface of plate 42, and such collection of liquid would interfere with accurate measurements.

It should of course be appreciated that other types of transducers and devices could be used within the broad scope of the present invention to measure impact of the fluid and, from this impact, determine the presence of liquid. Within this broad selection of elements for carrying out the invention, however, the structure illustrated in FIG. 2 has been found to be particularly useful.

It should be appreciated that a system has been provided for detecting and/or measuring liquid carryover in a gas stream such as a gas pipeline and the like. By prevention with this system the potential damage normally incurred due to liquid carryover can be avoided, and cost resulting in same can be tremendously reduced.

It is to be understood that the invention is not limited to the illustration described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

The invention claimed is:

1. A method for detecting liquid carry over in a gas stream, comprising the steps of:

obtaining a sample stream from said gas stream;

flowing said sample stream to an impactometer positioned along said sample line for being impacted by said sample, and for generating a signal indicative of sample density, wherein the sample density is obtained comparing to impactometer calibration data, and further comprising obtaining the impactometer calibration data using an inert gases of known density at given pressure and temperature conditions; and determining an amount of liquid in said sample stream from said signal.

2. The method of claim 1, wherein said impactometer has a flow inlet for said gas stream, and a separate flow outlet, and wherein said flow inlet is positioned to impact said stream onto a diaphragm of said impactometer.

3. The method of claim 2, wherein said flow inlet is substantially perpendicular to said diaphragm.

\* \* \* \* \*